United States Patent [19]

Muller et al.

[11] 4,336,335

[45] Jun. 22, 1982

[54] FERMENTATION PROCESS

[75] Inventors: Werner C. Muller, Dobbs Ferry, N.Y.; Franklyn D. Miller, Cincinnati, Ohio

[73] Assignee: National Distillers & Chemical Corp., New York, N.Y.

[21] Appl. No.: 152,239

[22] Filed: May 22, 1980

[51] Int. Cl.³ ................................................ C12P 7/06
[52] U.S. Cl. .................................. 435/161; 435/162; 435/313
[58] Field of Search ............... 435/161, 160, 813, 162, 435/163, 164, 165, 313, 316, 290

[56] References Cited

U.S. PATENT DOCUMENTS

| | | | |
|---|---|---|---|
| 1,759,122 | 1/1924 | Lichtenthaeler | 435/161 |
| 1,898,329 | 2/1933 | Wilson | 435/161 |
| 2,053,769 | 9/1936 | Dreyfus | 435/161 |
| 4,001,090 | 1/1977 | Kalina | 435/313 |
| 4,169,010 | 9/1979 | Marwil | 435/813 |

*Primary Examiner*—Raymond N. Jones
*Assistant Examiner*—John E. Tarcza
*Attorney, Agent, or Firm*—Kenneth D. Tremain

[57] ABSTRACT

Water soluble oxygenated hydrocarbons produced by microbial fermentation, e.g., ethanol, butanol, acetone, etc., are conveniently and economically recovered with a minimum expenditure of energy by passing heated by-product carbon dioxide gas through at least a portion of the fermentation medium to simultaneously vaporize and carry off oxygenated hydrocarbon fermentation product dissolved therein and reduce the temperature of the fermentation medium to a level conducive to maximum oxygenated hydrocarbon production. The vaporized oxygenated hydrocarbon fermentation product is separated from the carbon dioxide gas in a scrubbing unit and the resulting aqueous solution of product is concentrated, if desired, by distillation.

13 Claims, 2 Drawing Figures

FERMENTATION PROCESS

BACKGROUND OF THE INVENTION

1. Field of the Invention

This invention relates to processes for the production of water soluble oxygenated hydrocarbons, e.g., ethanol, butanol, acetone, etc. by batch or continuous fermentation.

2. Description of the Prior Art

With the ever-increasing depletion of economically recoverable petroleum reserves, the production of industrial chemicals and liquid fuels from vegetative sources becomes increasingly attractive. Thus, for example, in some areas, the economic and technical feasibility of using a 90% unleaded gasoline-10% anhydrous ethanol blend ("gasohol") has shown encouraging results. According to a recent study, gasohol powered automobiles have averaged 5% reduction in fuel compared to unleaded gasoline powered vehicles and have emitted one-third less carbon monoxide than the latter. In addition to offering promise as a practical and efficient fuel, biomass derived ethanol in large quantities and at a competitive price has the potential in some areas for replacing certain pertroleum-based chemical feedstocks. Thus, for example, ethanol can be catalytically dehydrated to ethylene, one of the most important of all chemical raw materials both in terms of quantity and versatility.

The various operations in processes for obtaining ethanol from such renewable sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentaion of sugar to a dilute solution of ethanol ("beer") and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy as possible so as to maximize the energy return for the amount of ethanol produced and enhance the standing of the ethanol as an economically viable replacement for petroleum based raw materials. To date, however, relatively little concern has been given to the energy requirements for manufacturing ethanol and other industrial chemicals from biomass and consequently, little effort has been made to minimize the thermal expenditure for carrying out any of the discrete operations involved in the manufacture of these important materials from vegetative sources.

In a typical ethanol fermentation process, an aqueous solution of fermentable substrate, i.e., dextrose, and a quantity of fermenting microorganisms, i.e., yeast cells, are introduced into one or the first of a series of fermentation vessels wherein the sugar is metabolically converted by the yeast into product ethanol and carbon dioxide gas. Since the metabolic evolution of ethanol is exothermic, provision is made for the cooling of the fermentation medium to maintain a range of temperature conducive to high levels of ethanol production, i.e., from about 68° F. to about 104° F. and preferably from about 68° F. to about 99° F. The resulting dilute solution of ethanol (so-called "beer") which can contain up to about 12 weight percent ethanol is thereafter subjected to distillation if the ethanol is to be recovered in a more concentrated form. Additional ethanol can be recovered from the gases, largely carbon dioxide containing relatively minor amounts of ethanol, which are evolved during fermentation by scrubbing the gases with water. The carbon dioxide once freed of ethanol is then discharged to the atmosphere. The foregoing description with appropriate changes in fermentable substrate and fermenting microorganism is generally applicable to the production of other water soluble oxygenated hydrocarbons such as butanol and acetone, the by-product carbon dioxide also being vented to the atmosphere. In some known fermentation processes, the by-product carbon dioxide is returned to the fermentation vessel in order to maintain agitation which will prevent the fermenting microorganisms and other insolubles from settling.

In the process described in U.S. Pat. No. 3,117,005, carbon dioxide from one end of an enclosed fermentation vessel (for the production of potable beer) is passed through a heater and humidifier and returned in the heated condition to the top of the vessel where it ruptures the cells of the foam, made up mainly of protein, which accumulates above the surface of the fermentation medium. The disrupted foam then sinks to become part of the homogeneous mass at the bottom of the fermentation vessel which is said to absorb objectional flavors from the product beer.

SUMMARY OF THE INVENTION

It has now been discovered that ethanol and other water soluble oxygenated hydrocarbons which can be volatilized at temperatures lower than the temperature of the fermentation process by which they are produced can be more efficiently recovered from the fermentation vessel with a significant saving of process energy by pressure within the fermentation vessel, scrubbing the carbon dioxide gas which evolves during fermentation with water to recover substantially all of the oxygenated hydrocarbon present therein as a dilute aqueous solution, heating the scrubbed carbon dioxide gas to a temperature above the temperature of the fermentation medium and passing the heated gas through at least a portion of fermentation medium to vaporize and carry off a substantial portion of the product water soluble oxygenated hydrocarbon dissolved therein. As the heated carbon dioxide gas flows through the cooler fermentation medium, the heat transferred to the fermentation medium results in the volatilization of dissolved water soluble oxygenated hydrocarbon. At the same time, volatilzation of the oxygenated hydrocarbon produces an evaporative cooling effect which serves to maintain the temperature of the fermentation medium within a range favoring maximum ethanol production. After recovery from the carbon dioxide gas in a scrubbing unit, the product oxygenated hydrocarbon present in dilute aqueous solution can be concentrated to any desired level employing any known technique such as distillation and advantageously is recovered by the distillation method which is disclosed herein and which represents a further aspect of the present invention. Optionally, the by-product carbon dioxide gas can be pressurized, preferably to at least 5 pounds above the pressure within the fermentation vessel, to facilitate its passage through the fermentation medium.

DESCRIPTION OF THE PREFERRED EMBODIMENTS

Figure 1:
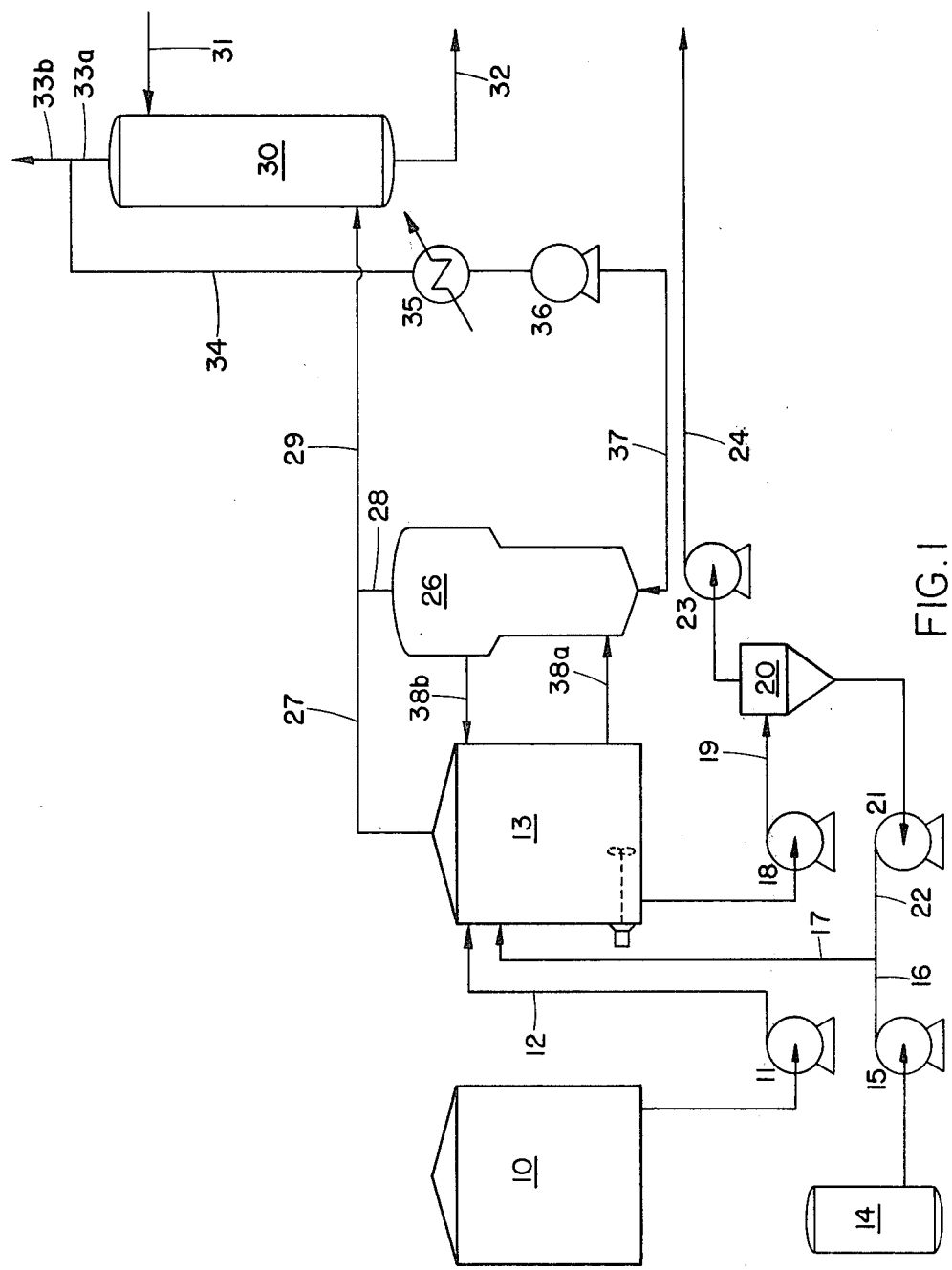
FIG. 1 is a diagrammatic flow sheet illustrative of an ethanol fermentation process in accordance with the present invention.

Referring to FIG. 1, a sterile aqueous solution of a fermentable sugar such as dextrose (glucose), fructose, maltose, sucrose or a mixture thereof containing from about 10 to about 40 weight percent sugar, and preferably from about 15 to about 25 weight percent sugar, is taken from vessel 10 which can be a storage vessel or a saccharification vessel in which the sugar is obtained by the enzymatic and/or acid hydrolysis of starch, and is delivered by pump 11 through line 12 to an agitated fermentation vessel 13 whose temperature is advantageously maintained at a level which favors maximum ethanol production. Fermentation vessel 13 is also provided with pH control and means for introducing nutrients and the small amounts of oxygen conventionally employed for maintaining proper yeast metabolism during fermentation. In the event the sugar solution contains more than 20 weight percent sugar, it is preferable to dilute the solution to about this level of sugar, advantageously with the nitrogen-rich spent mash obtained from the distillation process illustrated in FIG. 2 herein. The use of the spent mash possesses the two fold advantage of recycling nitrogen to the fermentation system which would otherwise be lost upon concentration of the ethanol during distillation, and reducing process water consumption by avoiding water build-up in the still bottoms. In addition to sugar, the foregoing solution can also contain significant amounts of partial starch hydrolysates (e.g., up to about 40 weight percent of the total carbohydrate present) which can be saccharified to fermentable sugar under the influence of saccharifying enzyme produced by the fermenting yeast and/or added saccharifying enzyme. A pumpable slurry of ethanol-producing yeast organisms free of contaminating organisms is conveyed from yeast storage tank 14 by pump 15 through lines 16 and 17 into fermentation vessel 13. The yeast in fermentation vessel 13 can be present at a level of from about 2 to about 8 weight percent of the fermentation medium (based on dry weight of yeast) and preferably is present at from about 3 to about 6 weight percent. Once steady state fermentation has been achieved, there will be no need to add more yeast since sufficient quantities of makeup yeast are grown in the fermentation vessel. The temperature of the fermentation medium is advantageously maintained at a level which provides maximum ethanol production, i.e., generally from about 68° F. to about 104° F. and preferably from about 86° F. to about 99° F. The pH of the fermentation medium is similarly regulated and can range from about 3.5 to about 5.5 and preferably from about 4.0 to 4.6. Dilute ethanol produced in fermentation vessel 13 containing a portion of the yeast cells therein is conveyed by pump 18 through line 19 to yeast separator/recovery unit 20 which separates substantially all of the yeast cells from the aqueous ethanol stream. Unit 20 can be a microfiltration device, centrifuge, etc. The yeast cells recovered in unit 20 are conveyed as a pumpable slurry or "cream" containing from about 10 to about 30 weight percent dry yeast and preferably from about 15 to about 25 weight percent dry yeast by pump 21 through lines 22 and 17 back into fermentation vessel 13. The fermentation medium essentially free of yeast cells and containing from 3 to 16, preferably 6 to 12, weight percent ethanol is transferred by pump 23 through line 24 onto storage or to a distillation unit for concentration of the ethanol. The carbon dioxide gas evolved by the fermentation medium in vessel 13 and containing some ethanol vapor is withdrawn from the vessel and conveyed through line 27, and together with the gaseous carbon dioxide and ethanol stream hich passes through line 28 from optional vaporization chamber 26, is introduced through line 29 to the base of scrubber 30. Cool water from the beer still bottoms supplied to the top of the scrubber through line 31 absorbs the ethanol present in the countercurrent flow of carbon dioxide gas resulting in a dilute solution of ethanol which is conveyed through line 32 to storage or to a distillation unit. The ethanol-free carbon dioxide gas is vented from scrubber 30 through line 33a with a portion of the gas being diverted through line 34 to be heated by heater 35, optionally pressurized by compressor 36, preferably to a pressure which is at least about 5 pounds greater than the pressure in fermentation vessel 13, and conveyed to the bottom of optional vaporization chamber 26 through line 37 with the remaining portion of carbon dioxide gas being vented to the atmosphere through line 33b. Contact of the heated carbon dioxide gas with the cooler cell-free fermentation medium in optional vaporization chamber 26 results in the transfer of heat to dissolved ethanol causing ethanol to evoporate and rise to the top of the chamber together with the by now cooler carbon dioxide gas. Due to the high volumetric flow rate of carbon dioxide through vaporization chamber 26, the density of the fermentation medium therein, supplied from fermentation vessel 13 through the line 38a, will be substantially less than the density of the fermentation medium in vessel 13. The density differences between vessels 13 and 26 will force a continuous flow, or circulation, of fermentation medium from one to the other vessel through lines 38a and 38b by application of the so-called hydraulic siphon effect. The evaporative cooling occurring in optional vaporization chamber 26 which will have an order of magnitude depending upon such factors as the volume and temperature of the incoming heated carbon dioxide gas, the volume and temperature of the liquid present in the chamber and the concentration of ethanol therein, will ordinarily be sufficient to provide a cooled liquid which, when returned to fermentation vessel 13 through line 38b, will maintain the temperature of the fermenting medium at the optimum level. These factors can be readily calculated for a given fermentation system employing known engineering principles.

Figure 2:
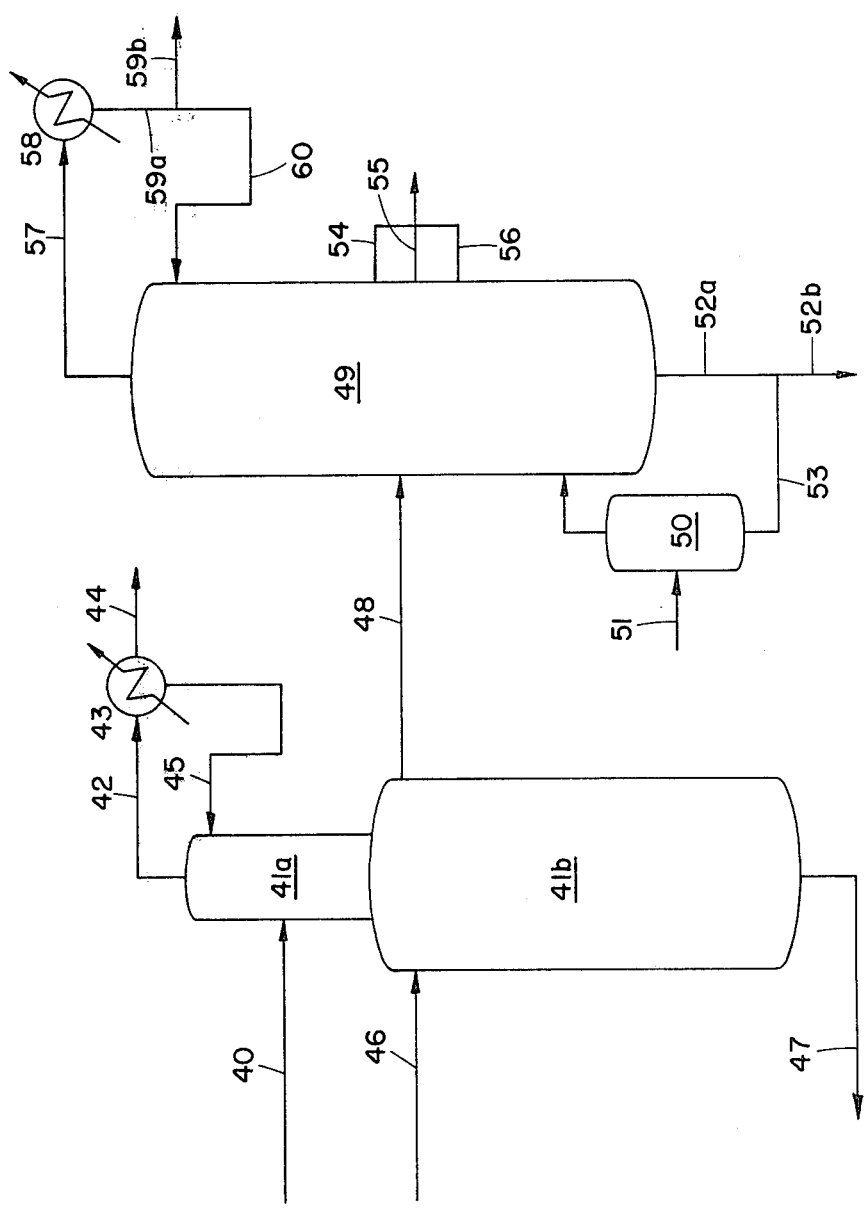
FIG. 2 is a diagrammatic flow sheet illustrative of an ethanol distillation process in accordance with the present invention employing as feed, the dilute aqueous ethanol ("beer") obtained in accordance with the fermentation process illustrated in FIG. 1.

Referring to FIG. 2, the aqueous ethanol solution obtained from the scrubber of FIG. 1 is introduced through line 40 to the upper portion of heads stripping column, 41a, with the vapor overheads being passed thrugh line 42 to condenser 43. Heads vapors are discharged through line 44 and the aqueous ethanol condensate is returned to column 41a through line 45 to serve as reflux. The main portion of the heads stripping column, 41b, is supplied through line 46 with the cell-free dilute aqueous ethanol fermentation medium obtaned from the fermentation vessel of FIG. 1. Spent mash is recovered from the bottom of the heads stripping column through line 47 where it can be advantageously added to the fermentation vessel of FIG. 1 as previously described. The aqueous ethanol stream fed to the heads stripping column, now substantially free of volatiles, is introduced through line 48 into rectifying column 49 driven with steam supplied to reboiler shell 50 through line 51. Spent water is removed from column 49 through line 52a with a portion thereof being recycled to the column through line 53 passing through reboiler shell 50 and with the remaining portion passing through line 52b. The water from line 52b is relatively pure and may be recycled to the fermentor or hydrolysis unit. Fusel oils are removed from column 49 through lines 54, 55 and 56 positioned at various levels of the column. The concentrated ethanol vapor at the head of the rectifying column is conveyed through lines 57 to condensor 58, with a portion of the 192 proof ethanol being conveyed through lines 59a and 60 to column 49 to serve as reflux and with the remaining portion being conveyed through line 59b to storage or to an anhydrous column for removal of residual water by azeotropic distillation.

What is claimed is:

1. In a process for producing a water soluble oxygenated hydrocarbon and by-product carbon dioxide gas from the exothermic fermentative action of a microorganism upon a substrate, wherein the improvement comprises scrubbing the by-product carbon dioxide gas with water to recover substantially all of the oxygenated hydrocarbon present therein as a dilute aqueous solution, heating the carbon dioxide gas to a temperature above the temperature of the fermentation medium, and passing the heated gas through at least a portion of fermentation medium to simultaneously vaporize and carry off oxygenated hydrocarbon present in said medium and reduce the temperature of the medium by the effect of evaporative cooling.

2. The process of claim 1 wherein the by-product carbon dioxide gas is pressurized prior to passage through the fermentation medium.

3. The process of claim 2 wherein the heated pressurized carbon dioxide gas is introduced into a portion of fermentation medium from which the fermenting mocroorganism has been removed and the cooled portion of fermentation medium is recombined with fermentation medium in which fermentation is actively taking place thereby cooling the latter.

4. The process of claim 1 wherein the water soluble oxygenated hydrocarbon which is produced is ethanol, the microorganism is an ethanol-producing yeast and the substrate is a fermentable sugar.

5. The process of claim 4 wherein the ethanol is concentrated by distillation.

6. The process of claim 5 wherein the nitrogen rich spent mash from the distillation is employed in the fermentation as a source of nutrient for the yeast.

7. A process for controlling the temperature of a fermentation medium in which water soluble oxygenated hydrocarbons and by-product carbon dioxide gas are produced by exothermic fermentation action of a microorganism upon a substrate, comprising scrubbing said by-product carbon dioxide gas with water to recover substantially all of the oxygenated hydrocarbon present therein as a dilute aqueous solution, heating the carbon dioxide gas to a temperature above the temperature of the fermentation medium, and passing the heated gas through at least a portion of fermentation medium to simultaneously vaporize and carry off oxygenated hydrocarbon present in said medium and reduce the temperature of the medium by the effect of evaporative cooling.

8. The process of claim 7 wherein the by-product carbon dioxide is pressurized prior to passage through the fermentation medium.

9. The process of claim 8 wherein the heated pressurized carbon dioxide gas is introduced into a portion of fermentation medium from which the fermenting microorganism has been removed and the cooled portion of fermentation medium is recombined with fermentation medium in which fermentation is actively taking place thereby cooling the latter.

10. The process of claim 7 wherein the water soluble oxygenated hydrocarbon which is produced is ethanol, the microorganism is an ethanol-producing yeast, the substrate is a fermentable sugar, and said controlled temperature range is from about 68° F. to about 100° F.

11. The process of claim 10 wherein said range is from about 86° F. to about 99° F.

12. The process of claim 10 wherein the ethanol is concentrated by distillation.

13. The process of claim 12 wherein the nitrogen rich spent mash from the distillation is employed in the fermentation as a source of nutrient for the yeast.

* * * * *